United States Patent
Karni et al.

[11] Patent Number: 5,970,983
[45] Date of Patent: *Oct. 26, 1999

[54] METHOD OF LASER SURGERY

[75] Inventors: Ziv Karni, Kfar Shemaryahu; Michael Kreindel, Haifa, both of Israel

[73] Assignee: ESC Medical Systems Ltd., Yokneam, Israel

[*] Notice: This patent is subject to a terminal disclaimer.

[21] Appl. No.: 08/904,249

[22] Filed: Jul. 31, 1997

Related U.S. Application Data

[63] Continuation-in-part of application No. 08/647,531, May 15, 1996, Pat. No. 5,655,547.

[51] Int. Cl.$^6$ .................................................. A61B 19/00
[52] U.S. Cl. ............................... 128/898; 606/3; 606/9; 606/16
[58] Field of Search ...................... 606/9–12, 3, 5, 606/2, 15, 16; 128/898

[56] References Cited

U.S. PATENT DOCUMENTS

| | | | |
|---|---|---|---|
| 4,408,602 | 10/1983 | Nakajima | 128/303.1 |
| 4,503,854 | 3/1985 | Jako | 128/303.1 |
| 5,139,494 | 8/1992 | Freiberg | 606/3 |
| 5,304,167 | 4/1994 | Freiberg | 606/3 |
| 5,387,211 | 2/1995 | Saadatmanesh et al. | 606/10 |
| 5,409,479 | 4/1995 | Dew et al. | 606/9 |

FOREIGN PATENT DOCUMENTS

WO 91/12766   9/1991   WIPO ........................................ 606/9

*Primary Examiner*—Mickey Yu
*Assistant Examiner*—Kelly O'Hara
*Attorney, Agent, or Firm*—Mark M. Friedman

[57] ABSTRACT

A method of laser surgery, comprising the steps of selecting lasers whose output radiation has appropriate extinction lengths in the tissue to be ablated, coagulated, and/or shrunk, and directing radiation from those lasers coaxially and substantially simultaneously at the tissue.

10 Claims, 2 Drawing Sheets

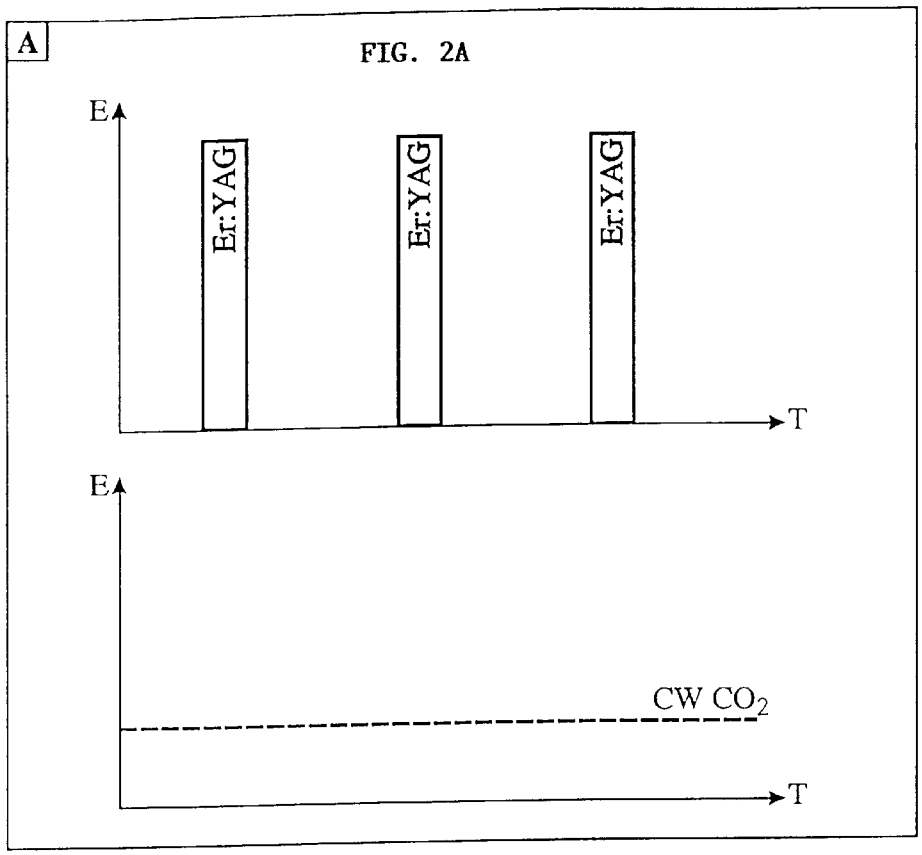
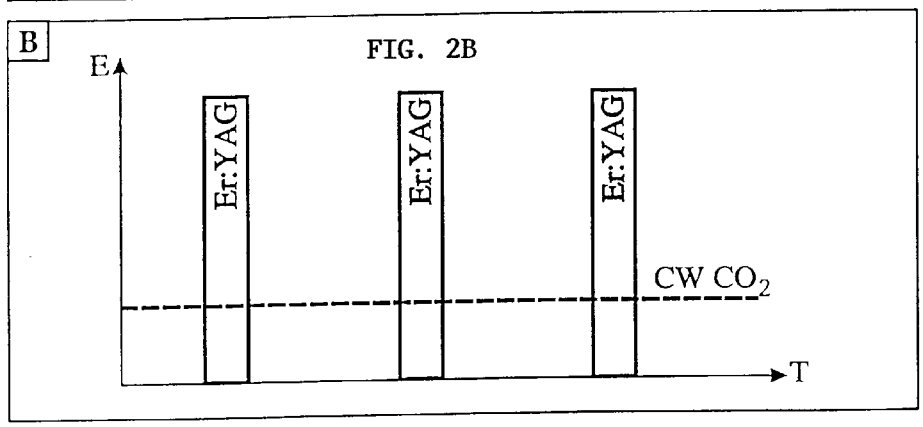
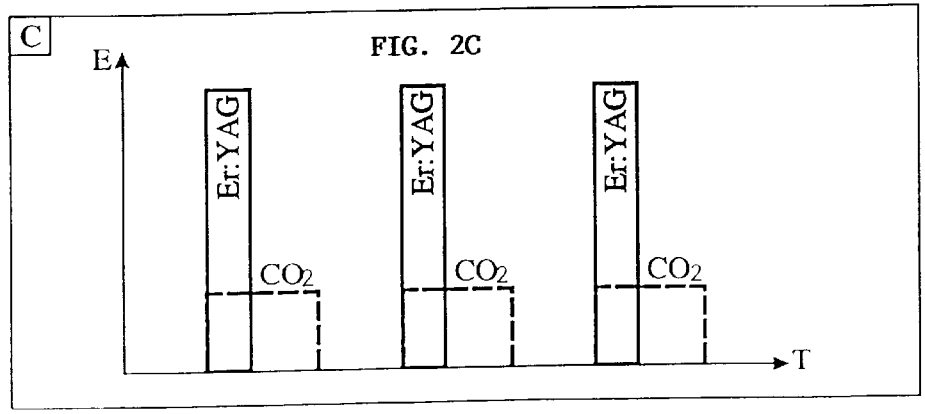

METHOD OF LASER SURGERY

This is a continuation-in-part of U.S. patent application Ser. No. 08/647,531, filed May 15, 1996, now U.S. Pat. No. 5,655,547.

FIELD AND BACKGROUND OF THE INVENTION

The present invention relates to a method for performing laser surgery and, more particularly, to a method for simultaneously ablating, coagulating, and/or shrinking biological tissue.

Directing coherent radiation from a laser at a target is a well known method for precisely cutting that target by ablating or vaporizing a portion of it. When the target is living biological tissue, the dynamic nature of the target poses special problems. For example, fluids such as blood may flow into the area of the cut, obscuring that area and absorbing part of the energy that otherwise would go into ablating the target.

This problem can be mitigated by directing beams of coherent radiation of two or more wavelengths at the tissue, one beam to ablate the tissue and the other to perform some other action, such as coagulating small blood vessels to prevent inflow of blood. For example, Freiberg, in U.S. Pat. No. 5,139,494, which is incorporated by reference for our purposes as if fully set forth herein, advocates using radiation in a range of wavelengths between about 0.1 and about 0.3 microns, and between about 2.0 and about 12.0 microns, for ablative cutting, and radiation in a range of wavelengths between about 0.3 microns and about 2.0 microns for coagulation. These beams of coherent radiation are directed coaxially at the tissue to be cut. Suitable means for combining laser beams coaxially are well known in the art. One such means is disclosed by Nakajima in U.S. Pat. No. 4,408,602. Another is disclosed by Jako in U.S. Pat. No. 4,503,854. Both of these patents are incorporated by reference for all purposes as if fully set forth herein.

Among the surgical procedures to which laser surgery may be applied are skin resurfacing and hair implantation. In skin resurfacing, the upper layer of skin is ablated by a first laser beam while the underlying collagen is coagulated and shrunk by a second laser beam. In hair implantation, the accuracy of the drilling of holes for the implantation of new hair using a first laser beam is enhanced by the use of a second laser beam to coagulate small blood vessels and prevent inflow of blood. Both of these procedures are very delicate and require precise selection and control of the wavelengths, intensities and durations of the laser beams.

There is thus a widely recognized need for, and it would be highly advantageous to have, a more precise method for using lasers to perform delicate surgical procedures such as skin resurfacing and hair implantation.

SUMMARY OF THE INVENTION

According to the present invention there is provided a method of revascularization of a myocardium, including the steps of: (a) selecting a first coherent radiation source that emits a first coherent radiation having an extinction length in the myocardium of between about 0.01 millimeters and about 0.001 millimeters; (b) selecting a second coherent radiation source that emits a second coherent radiation having an extinction length in the myocardium of between about 0.5 millimeters and about 0.01 millimeters; (c) ablating a first portion of the myocardium by directing a first beam of the first coherent radiation at the myocardium; and (d) coagulating a second portion of the myocardium by directing a second beam of the second radiation at the myocardium, substantially coaxially and substantially simultaneously with the first beam.

According to the present invention there is provided a method of performing surgery on soft dental tissue, including the steps of: (a) selecting a first coherent radiation source that emits a first coherent radiation having an extinction length in the soft dental tissue of between about 0.01 millimeters and about 0.001 millimeters; (b) selecting a second coherent radiation source that emits a second coherent radiation having an extinction length in the soft dental tissue of between about 0.1 millimeters and about 0.01 millimeters; (c) ablating the soft dental tissue by directing a first beam of the first coherent radiation at the soft dental tissue; and (d) coagulating the soft dental tissue by directing a second beam of the second radiation at the soft dental tissue, substantially coaxially and substantially simultaneously with the first beam.

The criteria for selecting the parameters for delicate laser surgery on skin tissue are the desired physical effects. The ablative laser beam should be strongly absorbed by the target tissue, so that the ablative effects of the laser beam are confined to the target tissue. Furthermore, the pulse duration should be shorter than the thermal relaxation time of the target tissue, to prevent thermal damage to adjacent tissue, while the pulse intensity should be sufficiently high to achieve the desired ablation. In skin resurfacing, the laser beam used to shrink the collagen should not be significantly absorbed in the overlying skin, but should be absorbed by the collagen. In hair implantation, the laser beam used should be absorbed only to an extent sufficient to coagulate the capillaries that are cut by the ablative laser beam.

The principles of the present invention also are applicable to transmyocardial revascularization and to surgical procedures on soft dental tissue, as discussed below.

The present invention successfully addresses the shortcomings of the presently known procedures for skin resurfacing, hair implantation, transmyocardial revascularization and dental surgery by providing an appropriate range of wavelengths, pulse durations, and pulse intensities for the laser beams used therein.

BRIEF DESCRIPTION OF THE DRAWINGS

The invention is herein described, by way of example only, with reference to the accompanying drawings, wherein:

FIG. 2A shows the firing schedule of the lasers in one embodiment of the present invention;

FIG. 2B shows the combined laser output corresponding to FIG. 2A;

FIG. 2C shows the combined laser output corresponding to the firing schedule of a different embodiment of the present invention.

DESCRIPTION OF THE PREFERRED EMBODIMENTS

Figure 1:
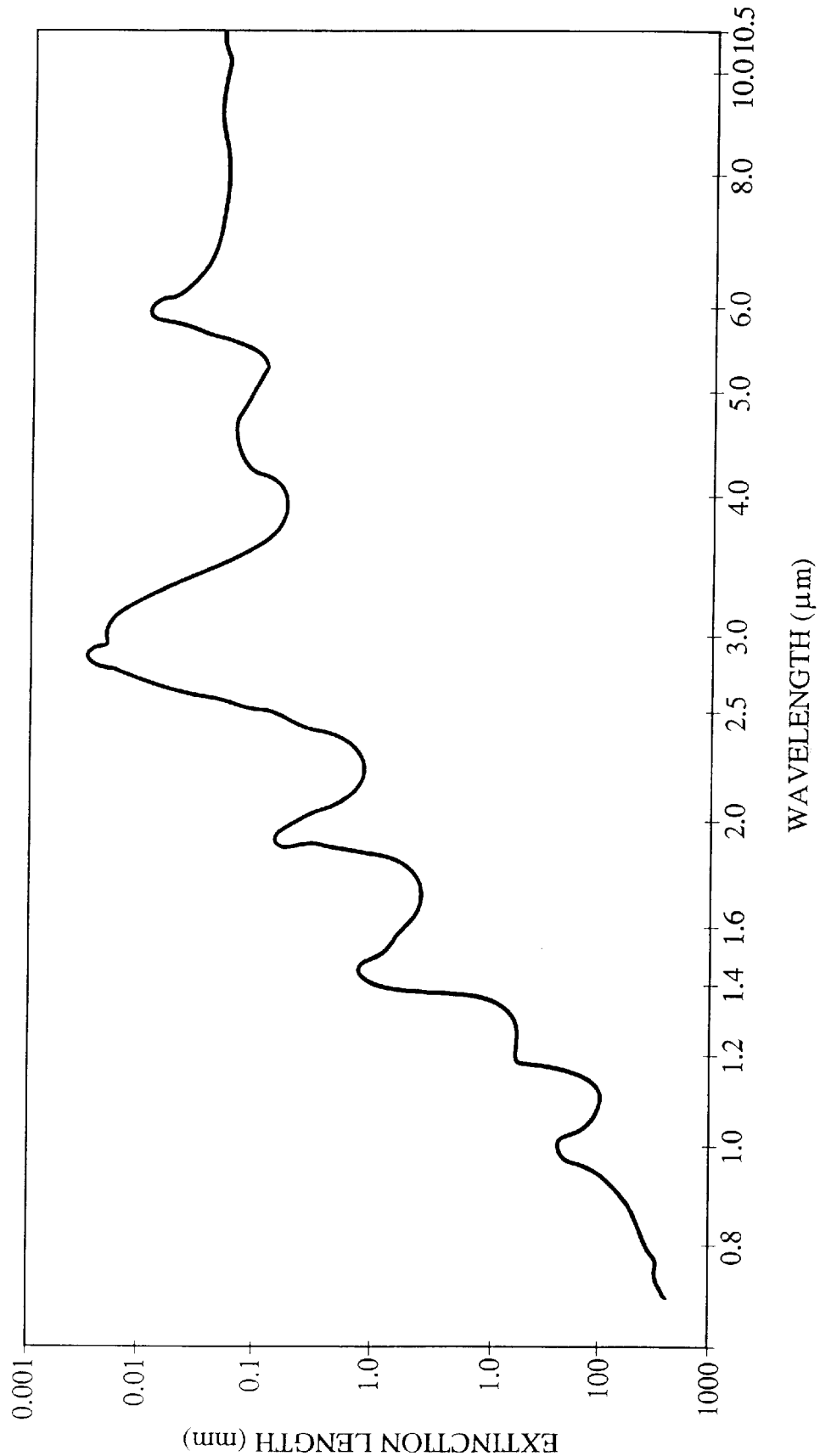
FIG. 1 is a graph of the extinction length, in water, of light of various wavelengths, vs. wavelength.

The present invention is of a method for delicate laser surgery. Specifically, the present invention can be used for precision skin resurfacing, hair implantation, transmyocardial revascularization and dental surgery. Although these specific procedures most commonly are performed on human patients, it will be appreciated by those ordinarily skilled in the art that the method described herein is equally applicable to surgical procedures carried out on lower mammals.

The principles of precision laser surgery according to the present invention may be better understood with reference to the drawings and the accompanying description.

Referring now to the drawings, FIG. 1 is a graph of the extinction length in water of infrared radiation of various wavelengths. Because soft tissue is 77% water by weight, water can be used as a proxy for tissue in selecting wavelengths for surgery.

To minimize peripheral damage to skin tissue, the extinction length of coherent radiation used for ablative cutting should be as small as possible. According to FIG. 1, this length is between 0.01 millimeters and 0.001 millimeters. Note that the corresponding range of wavelengths is between about 2.5 microns and about 3.2 microns. This range is substantially narrower than the 2–12 micron range recommended by Freiberg for ablative cutting. The 2.94 micron radiation of an erbium YAG laser has an extinction length in this range. The thermal relaxation time of an irradiated volume is on the order of $d^2/a$, where d is a characteristic length of the volume and a is a thermal diffusivity coefficient. In the case of mammalian tissue, a is about $1.4 \times 10^{-7}$ $m^2$/sec. It follows that the thermal relaxation time of mammalian tissue is approximately one millisecond. Thus, the laser pulse duration should be no longer than this, and preferably about 0.3 milliseconds. The energy density of each pulse preferably is between one Joule per square centimeter and 50 Joules per square centimeter.

The extinction length of coherent radiation used for coagulation of small blood vessels in the skin should be somewhat longer than the extinction length of coherent radiation used for ablation, to spread the heating effect of the laser beam over a larger depth range than is used for ablation. The intent here is merely to coagulate the blood, not to vaporize it. Between 0.1 millimeters and 0.01 millimeters is an appropriate extinction length for coagulation. The 10.6 micron radiation of a carbon dioxide laser has an extinction length in this range.

The laser beam used for coagulation may be either continuous or pulsed, as long as the duration of the coagulation beam substantially overlaps the duration of the ablation beam, as shown in FIGS. 2A, 2B, and 2C. In the four plots shown in these Figures, time T is the abscissa and beam intensity E is the ordinate. FIG. 2A shows separate firing schedules for an erbium YAG ablation laser and a carbon dioxide coagulation laser in a preferred embodiment of the present invention in which the carbon dioxide laser is a continuous wave laser. The erbium YAG laser emits periodic pulses. The carbon dioxide laser fires continuously. The total laser output is the superposition of these two outputs, as shown in FIG. 2B. Preferably, the power level of the carbon dioxide laser is sufficiently high to coagulate the blood vessels cut by the erbium YAG laser in between pulses of the erbium YAG laser, but not sufficiently high to cause peripheral damage by unwanted ablation. The preferred power density for a continuous wave carbon dioxide laser is between one Watt per square centimeter and 10 Watts per square centimeter.

FIG. 2C shows the combined output of the erbium YAG laser and the carbon dioxide laser in a preferred embodiment of the present invention in which both lasers are pulsed. Note that the duration of each carbon dioxide laser pulse overlaps, and extends substantially beyond, the duration of the corresponding erbium YAG laser pulse. Again, the object here is to coagulate the blood vessels cut by the erbium YAG laser without causing peripheral damage by unwanted ablation. The preferred carbon dioxide pulse duration is between one millisecond and 10 milliseconds, and the preferred power density is between one Watt per square centimeter and 100 Watts per square centimeter.

The extinction length of coherent radiation used to shrink collagen preferably should match the thickness of the target collagen layer, which may be as thick as about one millimeter. Collagen thinner than about 0.1 millimeters is shrunk by a laser appropriate for coagulation, for example a carbon dioxide laser. Thicker collagen is shrunk by a laser whose radiation has an extinction length of between about one millimeter and 0.1 millimeters. The 2.12 micron radiation of a holmium YAG laser has an extinction length in this range. The shrinkage laser beam may be continuous or pulsed. Preferred pulse durations for a holmium YAG laser used to shrink collagen are between 0.3 milliseconds and one millisecond, and the preferred pulse energy density is about one Joule per square centimeter.

The range of wavelengths useful for laser surgery, as shown in FIG. 1, is in the invisible infrared. In preferred embodiments of the present invention, a third, low power beam of visible coherent radiation is directed coaxially with the other two beams, so that the surgeon can see where the beams strike the patient.

As noted above, the principles of the present invention are applicable to transmyocardial revascularization, a procedure in which channels are drilled through the myocardium to allow blood from the chambers of the heart to circulate through the myocardium, in place of or to supplement the normal supply of blood to the myocardium via the coronary arteries. This procedure has long been done using a carbon dioxide laser. According to the present invention, two lasers are used for this purpose. The first laser is selected to produce coherent radiation with an extinction depth in the myocardial tissue of between 0.001 and 0.01 millimeters and with relatively high power, for ablation of the myocardial tissue to create the channels, with a minimum of peripheral damage. The second laser is selected to produce coherent radiation with an extinction depth in the myocardial tissue of between 0.01 millimeters and 0.5 millimeters and with relatively low power, for coagulation. As before, the preferred laser for ablation is an erbium YAG laser. The preferred laser for coagulation is either a carbon dioxide laser or a holmium YAG laser. A holmium YAG laser has the advantage of producing radiation that propagates through glass or quartz, so that optical fibers made of glass or quartz may be used to conduct the radiation to the surgical site. The radiation produced by an erbium YAG laser or by a carbon dioxide laser must be conducted to the surgical site by a hollow waveguide, or by optical fibers made of exotic materials such as crystalline silver halides. The firing of the coagulation laser continues after the firing of the ablation laser has stopped, in order to seal the outer ends of the channels and prevent leakage of blood from the heart.

It should be noted that an erbium YAG laser used alone would be suboptimal in transmyocardial revascularization, because the channels created by the laser would quickly fill with blood, and all of the energy of the laser would be absorbed in the evaporation of the blood, rather than in the desired ablation of myocardial tissue. It is for this reason that carbon dioxide lasers have been used almost exclusively for transmyocardial revascularization according to the prior art. According to the present invention, as the erbium YAG laser ablates the myocardial tissue, creating the channels, the carbon dioxide laser coagulates the channel walls, preventing inflow of blood. Thus, the channels are created with less peripheral damage than in the prior art.

Also as noted above, the principles of the present invention are similarly applicable to surgical procedures carried out on soft dental tissue. Again, a laser with an extinction depth of between 0.01 millimeters and 0.001 millimeters is used for ablation, and a laser with an extinction depth between 0.1 millimeters and 0.01 millimeters is used for coagulation. The laser of choice for ablation is an erbium YAG laser and the laser of choice for coagulation is a carbon dioxide laser.

The preferred parameter ranges for myocardial revascularization and dental surgery are:

|  | erbium YAG laser | carbon dioxide laser |
| --- | --- | --- |
| spot diameter | 0.1–2 mm | 0.1–2 mm |
| energy per pulse | 0.1–3 Joules | 0.1–1 Joule |
| pulse duration | 0.2–1 msec | 0.1–100 msec |
| repetition rate | 1–40 Hz | 1–200 Hz |

While the invention has been described with respect to a limited number of embodiments, it will be appreciated that many variations, modifications and other applications of the invention may be made.

What is claimed is:

1. A method of performing surgery on soft dental tissue, comprising the steps of:
   (a) selecting a first coherent radiation source that emits a first coherent radiation having an extinction length in the soft dental tissue of between about 0.01 millimeters and about 0.001 millimeters;
   (b) selecting a second coherent radiation source that emits a second coherent radiation having an extinction length in the soft dental tissue of between about 0.1 millimeters and about 0.01 millimeters;
   (c) ablating the soft dental tissue by directing a first beam of said first coherent radiation at the soft dental tissue; and
   (d) coagulating the soft dental tissue by directing a second beam of said second radiation at the soft dental tissue, substantially coaxially and substantially simultaneously with said first beam.

2. The method of claim 1, wherein said first coherent radiation source is a laser.

3. The method of claim 2, wherein said first coherent radiation source is selected from the group consisting of erbium YAG lasers, carbon dioxide lasers, and holmium YAG lasers.

4. The method of claim 1, wherein said second coherent radiation source is a laser.

5. The method of claim 4, wherein said laser is selected from the group consisting of carbon dioxide lasers and holmium YAG lasers.

6. The method of claim 1, wherein said first beam is pulsed.

7. The method of claim 6, wherein each of said pulses has a duration of between about 0.2 milliseconds and about one millisecond, an energy between about 0.1 Joules and about 3 Joules, and a spot diameter of between about 0.1 millimeters and 2 millimeters.

8. The method of claim 6, wherein said second beam is pulsed, said pulses of said second beam at least partially overlapping in time with said pulses of said first beam.

9. The method of claim 8, wherein each of said pulses of said second beam has a duration between about 0.1 milliseconds and about 100 milliseconds, an energy of between about 0.1 Joules and about 1 Joule, and a spot diameter of between about 0.1 millimeters and about 2 millimeters.

10. The method of claim 1, further comprising the step of directing a third beam of visible coherent radiation at the soft dental tissue, substantially coaxially and substantially simultaneously with said first beam.

* * * * *